(12) United States Patent
Vargas et al.

(10) Patent No.: US 11,505,510 B2
(45) Date of Patent: Nov. 22, 2022

(54) BIOLOGICAL INOCULANT HAVING ENHANCED FERTILIZING AND FUNGICIDAL ACTIVITY

(71) Applicant: YPF TECNOLOGÍA S.A., Ciudad Autónoma de Buenos Aires (AR)

(72) Inventors: Walter Alberto Vargas, La Plata (AR); Sebastián Reinoso, La Plata (AR); María Cecilia Orsini, La Plata (AR); Sebastián Alejandro Trejo, Ensenada (AR); Eliana Abrahamovich, La Plata (AR)

(73) Assignee: YPF TECNOLOGIA S.A., Ciudad Autónoma de Buenos Aires (AR)

( * ) Notice: Subject to any disclaimer, the term of this patent is extended or adjusted under 35 U.S.C. 154(b) by 93 days.

(21) Appl. No.: 16/534,139

(22) Filed: Aug. 7, 2019

(65) Prior Publication Data

US 2020/0048157 A1 Feb. 13, 2020

Related U.S. Application Data

(60) Provisional application No. 62/715,506, filed on Aug. 7, 2018.

(51) Int. Cl.
*A01N 63/30* (2020.01)
*C05G 3/60* (2020.01)
*C05F 11/08* (2006.01)
*A01N 63/00* (2020.01)

(52) U.S. Cl.
CPC .............. *C05F 11/08* (2013.01); *A01N 63/00* (2013.01); *A01N 63/30* (2020.01); *C05G 3/60* (2020.02)

(58) Field of Classification Search
CPC ......... C05F 11/08; A01N 63/30; A01N 63/00; A01N 63/38; C05G 3/60; C12R 2001/885; C12N 1/145; C12N 1/20; C12N 1/14; A01C 1/00
See application file for complete search history.

(56) References Cited

U.S. PATENT DOCUMENTS

2011/0027232 A1* 2/2011 Harman ................. A01N 63/20
424/93.4

OTHER PUBLICATIONS

Brotman Y. et al, Trichoderma-Plant Root Colonization: Escaping Early Plant Defense Responses and Activation of the Antioxidant Machinery for Saline Stress Tolerance, 2013 PLoS Pathog, 9(3): e1003221. (Year: 2013).*
Sivparsad, B. et al, Comparative evaluation of commercial rhizobial inoculants of soybean, 2016, South African Journal of Plant and Soil, 33:2, 157-160. (Year: 2016).*
Woo, S. L. et al, Trichoderma-based Products and their Widespread Use in Agriculture, 2014, The Open Mycology Journal, 8; 71-126 (Year: 2014).*
Shah, M. J. et al, Bio-control of Root Rot of Brinjal Caused by Rhizoctonia solani Kuhn, 2018, International Journal of Current Microbiology and Applied Sciences, 7(3): 2469-2474 (Year: 2018).*
Al-Hazmi, A. et al, Effects of different inoculum densities of Trichoderma harzianum and Trichoderma viride against Meloidogyne javanica on tomato, 2016, Saudi Journal of Biological Sciences, 23(2): 288-292 (Year: 2016).*
Zafari, Doustmorad, Ayoubi, Najmeh, and Mirabolfathi, Mansore, "Application of *Trichoderma* species and Bradyrhizobium japonicum against Phytophthora sojae in vivo" World Academy of Science, Engineering and Technology, 2011, pp. 908-914 vol. 74.

* cited by examiner

*Primary Examiner* — Olivia M. Wise
*Assistant Examiner* — Anjali Ajit Hirani
(74) *Attorney, Agent, or Firm* — Muncy, Geissler, Olds & Lowe, P.C.

(57) ABSTRACT

A biological inoculant having both fertilizing and fungicidal activity is disclosed. More particularly, a bio-inoculant having the said combined effects, comprising *Bradyrhizobium japonicum* and specific isolates from the *Trichoderma* genus is disclosed. The bio-inoculant is applied to soybean crops for preventing fungi borne diseases. More particularly, the bio-inoculant of the invention is useful for protecting soybean crops against infection by *Fusarium* sp., *Colletotrichum* sp., *Cercospora* sp., *Sclerotinia* sp. and *Rhizoctonia* sp.

6 Claims, 4 Drawing Sheets
(3 of 4 Drawing Sheet(s) Filed in Color)
Specification includes a Sequence Listing.

BIOLOGICAL INOCULANT HAVING ENHANCED FERTILIZING AND FUNGICIDAL ACTIVITY

FIELD OF THE INVENTION

The present invention generally relates to the field of agricultural technology for enhancing the performance of industrial crops. In particular, the invention refers to a biological inoculant having both fertilizing and fungicidal activity, which enhances crop plants' growth and yield. More particularly, the present invention relates to a bio-inoculant having the said combined effects, comprising *Bradyrhizobium japonicum* and specific isolates from the *Trichoderma* genus. In a particular embodiment of the invention, the bio-inoculant is applied to soybean crops for preventing fungi borne diseases. More particularly, the bio-inoculant of the invention is useful for protecting soybean crops against infection by *Fusarium* sp., *Colletotrichum* sp., *Cercospora* sp., *Sclerotinia* sp. and *Rhizoctonia* sp.

BACKGROUND OF THE INVENTION

All over the world millions of hectares are sown every year for soybean. The different sown areas span diverse environments, where plants may be exposed to several phytopathogens affecting the crop yield.

Normally, crops are exposed to a great number of diseases having a strong impact on the harvest yield. The way for addressing these issues currently relies on the use of chemical pesticides. However, these decrease the quality of the environment and compromise the farmer's health. In addition to the significant direct effects of agrochemicals on the environment, their disproportionate use is another relevant aspect to be taken into account, especially considering that it promotes the developing of resistance in the targeted organisms. The consequence of this effect has a major impact since aggressive agents must progressively be used on the pathogenic microorganisms, which in turn results in an increasing aggressiveness on the environment and the farmer. Therefore, the development of new strategies for controlling phytopathogens that can guarantee crop health is of global interest, especially without compromising the ecological integrity of the environment while reducing their impact on human health.

Currently, national and international sectors of agribusiness have placed a considerable interest on the development of pest control products of biological origin for addressing plant diseases. Soybean is one of the most economically important crops in countries with a high developed agricultural industry. During the 2016 period, in Argentina for instance, more than 21 million hectares were sown, implying a huge market demand for the use of phytopathological control agents. Therefore, the development of a new generation of inoculants for addressing this pest issue has a great demand potential in agribusiness.

*Trichoderma* comprises a genus of filamentous fungi that inhabit the soil, and pose significant benefits to the biotechnological industry, ranging from the production of enzymes with industrial significance to their use for biological control of crop diseases. The potential of *Trichoderma* in the field of agricultural industry is based on its antagonistic capacity for pathogenic agents, including other filamentous fungi.

As such, *Trichoderma* strains may exert biological control via three combined mechanisms of action: mycoparasitism, antibiosis and niche competition (Harman et al. (2004) *Trichoderma species—opportunistic, avirulent plant symbionts*. Nature Reviews Microbiology, 2, 43-56; Druzhinina et al. (2011) *Trichoderma: the genomics of opportunistic success*. Nature Reviews Microbiology, 9, 749-759) The joint action of these three mechanisms gives *Trichoderma* a considerable advantage over chemical fungicidal agents, since it is not directed to a single point of action in pathogens, but instead displays a synergic effect at the structural, physiological and nutritional levels.

The use of *Trichoderma*-based biopesticides has been promoted throughout Europe, Australia and the USA. In Argentina, for example, the company Rizobacter has launched a product, the active ingredient of which is a *Trichoderma harzianum* isolate, which has shown effective biocontrol capacity for the most significant diseases in wheat and barley crops.

The effectiveness of *Trichoderma* strains and their application for protecting crop health has been known for decades and several advanced genetic studies are known as well as the genomic sequences of the most industrially relevant strains.

However, it is also a concern that biological agents for controlling pests produce broad-spectrum antimicrobial compounds that would inhibit the normal development of bacteria that are beneficial to the soil quality, including *Bradyrhizobium japonicum*.

Peptaibols, polyketides, pyrones, terpenes and diketopiperazine-like compounds are the main antimicrobial compounds produced by *Trichoderma* isolates. These compounds are known to counteract bacterial growth, including those microorganisms considered as beneficial species to plants (Rosa Hermosa, Rosa Elena Cardoza, Maria Belén Rubio, Santiago Gutiérrez, Enrique Monte, *Secondary Metabolism and Antimicrobial Metabolites of Trichoderma*, Chapter 10 in *Biotechnology and Biology of Trichoderma*, $1^{st}$ Edition, Elsevier, 2014).

In addition, light, high temperatures and humidity affect conidia viability. Currently available bio-fungicidal agents are formulated based on conidial suspensions which display a limited viability of the final pest-controlling product, due to degradation of conidia, which turns the fungal agent ineffective.

Particularly, the formulation of the biological inoculant of the invention allowed an amount of $10^9$ conidia per milliliter, and its pest control efficiency was verified in serial dilutions of up to $10^6$ conidia/ml. Said concentrations provide an advantage over biological agents known to date and also allow for a broader viability window in the formulations.

Nonetheless, although it is not possible to foresee the impact of previously mentioned antimicrobial secreted compounds, the present inventors have found an adequate and effective combination of biological agents, providing enhanced pest control activity and at the same time promoting plant growth.

To the inventors' knowledge, no combination of beneficial bacteria and biological antifungal agents has been considered to date that successfully applies to crop fields. In particular, there are no biological inoculants available that provide both fertilization and antifungal activities, useful for agricultural crops of economic interest.

Due to the inventors' strategy for isolation, culture and selection, the present invention allowed the generation of a highly efficient bio-controller reaching a high standard for simultaneous control of five of the most aggressive plant pathogens for soybean. This is consistent with the low dose required to achieve the expected results in field trials (1 ml/Kg seed) at a concentration of $10^6$ spores/ml. The results reached by the present invention exceeds those obtained by Zafari et al. (Zafari et al. 2011. *Application of Trichoderma species and Bradyrhizobium japonicum against Phytophthora sojae in vivo*. World Academy of Science, Engineering and Technology 74) where only *Phytophtora sojae* is being controlled. In addition, the scheme of inoculation in Zafari et al. uses a dose of 80 ml/kg of seed and the formulation is amended with CMC. The strategy developed in the present invention allowed the use of 1 ml/Kg of seeds of a non-amended inoculant, i.e., a significantly lower dose, while reaching a broad range of pathogen control.

Therefore, the present invention acknowledges the current need for a biofungicide developed for extensive farming and effective crop biofertilization, which also protects agricultural crops of interest against fungal infection, and at the same time allows for a cost-effective, safe and easy-to-use formulation having a high commercial durability and longer viability.

SUMMARY OF THE INVENTION

The present invention describes a biological inoculant for controlling phytopathogens, which contributes in fighting the main plant pests having great impact on agricultural crops, more preferably soybean, and also in reducing the use of chemical pesticides.

Accordingly, the first object of the present invention is a biological inoculant comprising: a) *Bradyrhizobium japonicum*; and b) a *Trichoderma harzianum* strain, wherein the *Trichoderma harzianum* strain comprises an intergenic region of the 18S rRNA gene sequence selected from the sequences set forth in SEQ ID NO: 1, SEQ ID NO: 2 and SEQ ID NO: 3.

In a preferred embodiment of the present invention the biological inoculant comprises a) *Bradyrhizobium japonicum*; and b) a *Trichoderma harzianum* strain comprising an intergenic region of the 18S rRNA gene sequence as set forth in SEQ ID NO: 1.

In a more preferred embodiment of the invention, the *Trichoderma harzianum* strain comprising an intergenic region of the 18S rRNA gene sequence as set forth in SEQ ID NO: 1, is a *Trichoderma harzianum* strain which was deposited at the ATCC on May 20, 2019, under Accession Number PTA-125914.

Consequently, the present invention discloses a *Trichoderma harzianum* strain culture having Accession Number PTA-125914, deposited at the ATCC on May 20, 2019.

The bio-inoculant of the present invention exerts a combined action of biofertilization and biological control. This mixed bio-inoculant formulation comprises *Bradyrhizobium japonicum* and a fungicidal agent of the *Trichoderma* genus.

According to an embodiment of the biological inoculant of the invention, *Bradyrhizobium japonicum* is formulated as a water-based extract and the *Trichoderma harzianum* strain is added to the *B. japonicum* extract as a conidial suspension having a final concentration of $10^6$-$10^9$ spores/ml. The inoculant mixture may contain culture medium remnants including $KH_2PO_4$, $K_2HPO_4$, $MgSO_4 \cdot 7H_2O$, NaCl, $CaCl_2$, $KNO_3$, $(NH_4)_2HPO_4$, Glycerin, molasses, yeast extract, and, bio-polymeric and glucosidic compounds.

It is also another object of the invention to provide a use of the claimed biological inoculant for protecting agricultural crop plants against the infection by phytopathogenic fungi.

Preferably, the crop plants are selected from soybean, wheat, maize, sunflower, cotton, sorghum, alfalfa, flax, canola, chickpea, rice, potato, onion, yerba mate (*Ilex paraguariensis*), tea and vine.

In a more preferred embodiment, the phytopathogenic fungi may be selected, without limitation, from the group consisting of *Fusarium* sp., *Colletotrichum* sp., *Cercospora* sp., *Sclerotinia* sp., and *Rhizoctonia* sp. More preferably, the phytopathogenic fungi are selected from the group consisting of *Fusarium tucumaniae*, *Colletotrichum truncatum*, *Cercospora sojina*, *Sclerotinia sclerotiorum*, and *Rhizoctonia solani*.

The present invention also provides a method for protecting agricultural crop plants against the infection by phytopathogenic fungi, said method comprising applying the biological inoculant to the seeds of agricultural crop plants before cultivation.

Preferably, in the method for protecting agricultural crop plants against the infection by phytopathogenic fungi, the crop plants are selected from soybean, wheat, maize, sunflower, cotton, sorghum, alfalfa, flax, canola, chickpea, rice, potato, onion, yerba mate (*Ilex paraguariensis*), tea and vine.

In a preferred embodiment of the method for protecting agricultural crop plants against the infection by phytopathogenic fungi, the phytopathogenic fungi may be selected, without limitation, from the group consisting of *Fusarium* sp, *Colletotrichum* sp., *Cercospora* sp, *Sclerotinia* sp., and *Rhizoctonia* sp. More preferably, the phytopathogenic fungi are selected from the group consisting of *Fusarium tucumaniae*, *Colletotrichum truncatum*, *Cercospora sojina*, *Sclerotinia sclerotiorum*, and *Rhizoctonia solani*.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following figures form part of the present specification and are included to further illustrate certain aspects of the present invention, without limiting the scope thereof.

DETAILED DESCRIPTION OF THE INVENTION

Figures 1A, 1B, 1C:
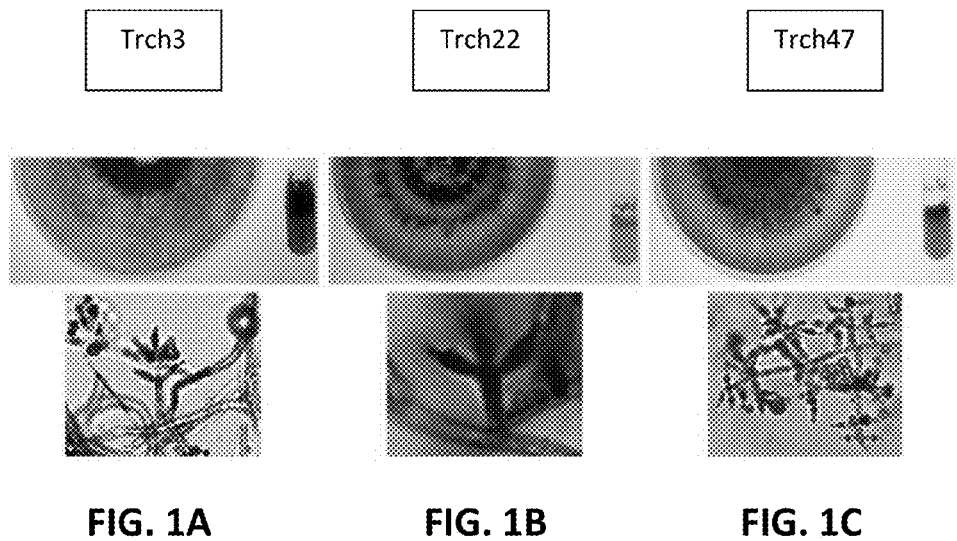
FIG. 1. Micro- and macroscopic characterization of three relevant *Trichoderma* isolates. Photographs of the colonies grown in potato dextrose agar (PDA) medium are shown for each *Trichoderma* strain A) Trch3, B) Trch22 and C) Trch47, where the distinctive green coloration of the genus may be seen, as well as the growth patterns in concentric halos. The inserted micrographs show hyaline and branched conidiophores. Bottle-shaped phialidae may also be observed being attached perpendicular to conidiophores.

The present application discloses a biological inoculant having both fertilizing and fungicidal activity. More particularly, said bio-inoculant has the abovementioned combined effects, and consists of a fertilizer and a pesticide, both of biological origin. More specifically, the bio-inoculant of the present invention comprises *Bradyrhizobium japonicum* and a specific isolate from the *Trichoderma* genus.

As discussed above herein, the present inventors sought for a biological control agent for protecting agricultural crop plants against the infection by phytopathogenic fungi, including those responsible for the most renowned diseases in many agricultural crops of relevance, such as crops selected from soybean, wheat, maize, sunflower, cotton, sorghum, alfalfa, flax, canola, chickpea, rice, potato, onion, yerba mate (*Ilex paraguariensis*), tea and vine. More preferably, the agricultural crop to be protected against a phytopathogenic infection is soybean.

In particular, protection is exerted against infection by pathogens from the genera *Fusarium* sp., *Colletotrichum* sp., *Cercospora* sp., *Sclerotinia* sp., and *Rhizoctonia* sp. Yet more particularly, protection is exerted against infection by *Fusarium tucumaniae*, *Colletotrichum truncatum*, *Cercospora sojina*, *Sclerotinia sclerotiorum*, and *Rhizoctonia solani*.

The present inventors carried out extensive research and were able to generate numerous *Trichoderma* isolates from the soil of agriculturally relevant crop plants, in particular, soybean. A total of 60 *Trichoderma* isolates were obtained from the roots of crop plants as well as from soil samples. Subsequently, fungal isolates were identified by morphology and colony pigmentation. Also, identification of distinctive structures of the genus was carried out using microscopy techniques. The isolated strains were further selected after continuous rounds of growth and selection by their capacity to simultaneously control five of the most relevant pathogens for soybean plants: *Fusarium tucumaniae*, *Colletotrichum truncatum*, *Cercospora sojina*, *Sclerotinia sclerotiorum*, and *Rhizoctonia solani*.

In order to determine the genus and species of the selected *Trichoderma* isolates, methodologies based on molecular biology were used to identify the barcode system of the internal transcribed spacer (ITS) region (Druzhinina et al., 2005. *An oligonucleotide barcode for species identification in Trichoderma and Hypocrea*. Fungal genetics and biology, FG & B. 42. 813-28. 10.1016/j.fgb.2005.06.007). Upon assessment of the obtained genomic sequences, by sequence alignment and comparison of the sequences determined for intergenic regions of the 18S rRNA gene (SEQ ID NO: 1, SEQ ID NO: 2 and SEQ ID NO: 3), it was concluded that the three identified *Trichoderma* isolates referred to as Trch3, Trch22 and Trch47, respectively, correspond to strains of *Trichoderma harzianum* that show significant antagonistic activity against pathogenic microorganisms, i.e., these strains have fungicidal properties.

Observation of the isolates allowed the identification of aerial mycelia in them; also, green ellipsoidal conidia were produced from effused and branched conidiophores, with regularly paired phialides.

Based on the experimental assays carried out by the inventors on three selected isolates, it was shown that these *Trichoderma* strains are not inhibitory of the growth of some of the beneficial bacteria found in soil. Particularly, the selected *Trichoderma* strains enable *Bradyrhizobium*, *Pseudomonas*, *Azospirillum* and *Bacillus* growth, and promote satisfactory development of agricultural crop plants at risk of infection by phytopathogenic fungi.

According to the invention, the bio-inoculant comprises *Bradyrhizobium japonicum* and a *Trichoderma harzianum* strain, wherein the *Trichoderma harzianum* strain comprises an intergenic region of the 18S rRNA gene sequence selected from SEQ ID NO: 1, SEQ ID NO: 2 and SEQ ID NO: 3.

Particularly, the formulation of the biological inoculant of the invention allowed an amount of $10^9$ conidia per milliliter, and its pest control efficiency was verified in serial dilutions of up to $10^6$ conidia/ml. Said concentrations provide an advantage over biological agents known to date and also allow for a broader viability window in the formulations.

Also, the present invention relates to a use of the claimed biological inoculant for protecting agricultural crop plants against the infection by phytopathogenic fungi, as well as to a method for the biological control of phytopathogenic fungi in agricultural crop plants, comprising the application of an inoculant according to the invention to the seeds of the crop of interest.

Below, experimental assays are described for better understanding how to take into practice the present invention.

EXAMPLES

The invention will now be further described based on the following examples. It is to be understood that these examples are intended for illustrative purposes only, and by no means should be construed to be limiting the scope of the invention, which is only defined by the appended claims.

Example 1

Determination of Antagonist Capacity of Isolated Trichoderma Strains

As described herein before, a total of 60 *Trichoderma* isolates were obtained from the roots of crop plants as well as from soil samples. These samples were identified by morphology, colony pigmentation and identification of distinctive structures of the genus by microscopy techniques.

In order to determine the antagonistic activity of the soil isolates, confrontation assays were performed with a series of phytopathogenic fungi, including those responsible for the most renowned diseases in plant crops: *Fusarium* sp, *Colletotrichum* sp., *Cercospora* sp., *Sclerotinia* sp., and *Rhizoctonia* sp.

These genera of fungal pathogens affect many agronomically relevant crops, such as soybean, wheat, maize, sunflower, cotton, sorghum, alfalfa, flax, canola, chickpea, rice, potato, onion, yerba mate (*Ilex paraguariensis*), tea and vine.

During several growth rounds in the presence of the above mentioned fungal pathogens, 60 *Trichoderma* isolates were challenged and selected for their abilities to simultaneously control the five above mentioned pathogens. Out of the 60 tested isolates, three were selected which presented antagonistic activity against all the tested phytopathogens. After this in vitro selection protocol, the three isolated *Trichoderma* strains with increased biocontrol capabilities, referred to herein as: Trch3, Trch22 and Trch47, were identified as *Trichoderma harzianum* strains comprising an intergenic region of the 18S rRNA gene sequence selected from SEQ ID NO: 1, SEQ ID NO: 2 and SEQ ID NO: 3, respectively.

Micro- and macroscopic characterization of said three isolated *Trichoderma* strains was performed by growing colonies on solid media, using potato dextrose agar (PDA).

The distinctive green coloration of the *Trichoderma* genus was observed in the different Petri dishes, along with growth patterns in concentric halos. The micrographs corresponding to three relevant *Trichoderma* isolates of the invention as shown in FIG. 1 confirm the presence of hyaline and branched conidiophores. Also, bottle-shaped phialidae were observed being attached perpendicularly to conidiophores.

Figure 2:
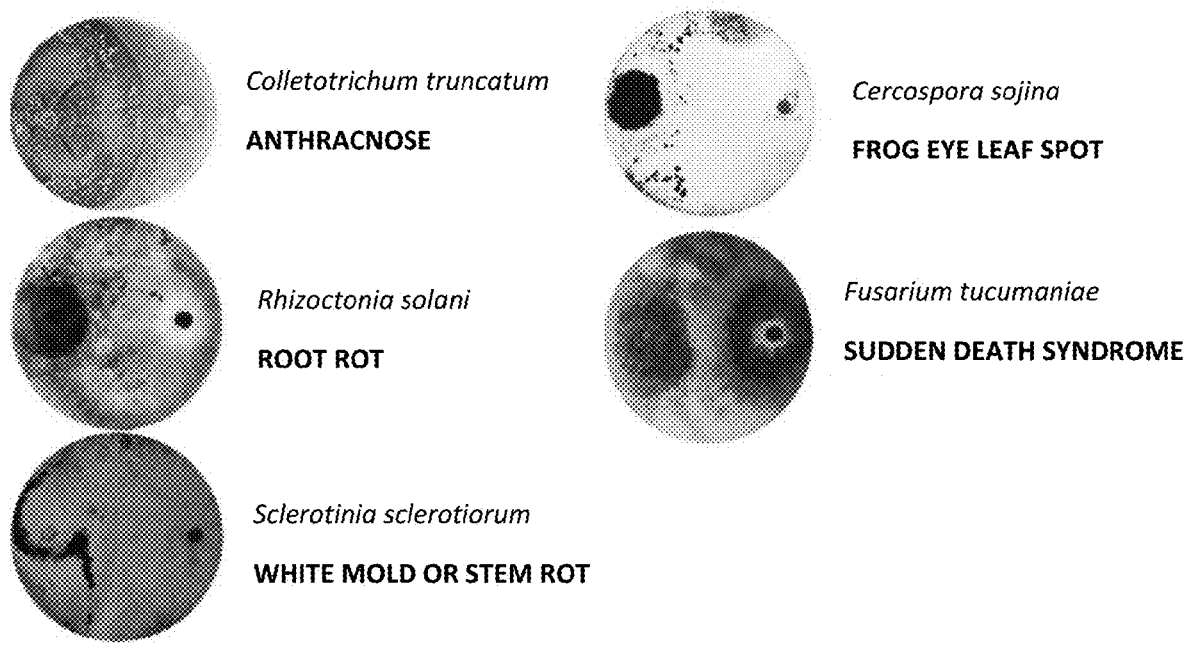
FIG. 2. Confrontation assays in Trch3 cultures were carried out by exposing the strain to five agriculturally relevant pathogens. In all cases, *Trichoderma* hyphae may be observed growing over the pathogenic fungus, stopping the pathogen's growth and even neutralizing it, as in the case of *S. sclerotinium*).

Confrontation assays were carried out using Trch3 culture and exposing the strain to five agriculturally relevant pathogens. FIG. 2 shows *Trichoderma* colony overgrowing the pathogenic fungi, stopping the pathogen's growth and even neutralizing it, as in the case of *S. scletiorum*. Similar results were obtained with the other two selected strains, Trch22 and Trch47 (not shown).

It was concluded that these three strains had a high efficiency for the biological control of soybean diseases derived from phytopathogenic fungi infection.

Example 2

Characterization of Interaction of Isolated Trichoderma Strains with Soybean The effects of the three isolated *Trichoderma* strains on the growth of soybean plants in greenhouse conditions were determined. In order to achieve this, the most effective isolated strains for controlling the proliferation of pathogenic fungi were selected and the concentration of conidia to inoculate plants was optimized (Samuels & Hebbar, 2015). The biological inoculant was established to be still efficient at a concentration as low as $10^6$ spores/ml.

Later assays demonstrated that the selected three *Trichoderma harzianum* strains colonize the roots of soybean plants in the presence of *B. japonicum* without reducing their natural nodulation capacity. Moreover, treatment of soybean seeds with these *T. harzianum* strains even resulted in an increase in the number of nodules per root weight, with Trch3 displaying the greater effect, and also maintaining the ratio of functional nodules per plant. Table 1 below shows the results obtained in this experiment with soybean plants treated with the selected *Trichoderma harzianum* strains, designated herein as Trch3, Trch22 and Trch47.

TABLE 1

Root development and natural nodulation of soybean plants treated with strains Trch3, Trch22 and Trch47. Strains were inoculated in soybean seedlings and the different parameters were assessed when plants developed the fifth tripholium. Control plants are soybean plants receiving no treatment.

|         | Root weight  | Nodules/gr root | Functional (%) |
|---------|--------------|-----------------|----------------|
| Control | 1.4 ± 3 gr   | 24.5 ± 5        | 70 ± 10        |
| Trch3   | 1.9 ± 3 gr   | 34.9 ± 10       | 71 ± 5         |
| Trch22  | 1.7 ± 2 gr   | 27.4 ± 5        | 80 ± 10        |
| Trch47  | 1.8 ± 4 gr   | 31.8 ± 8        | 75 ± 8         |

Figure 3:
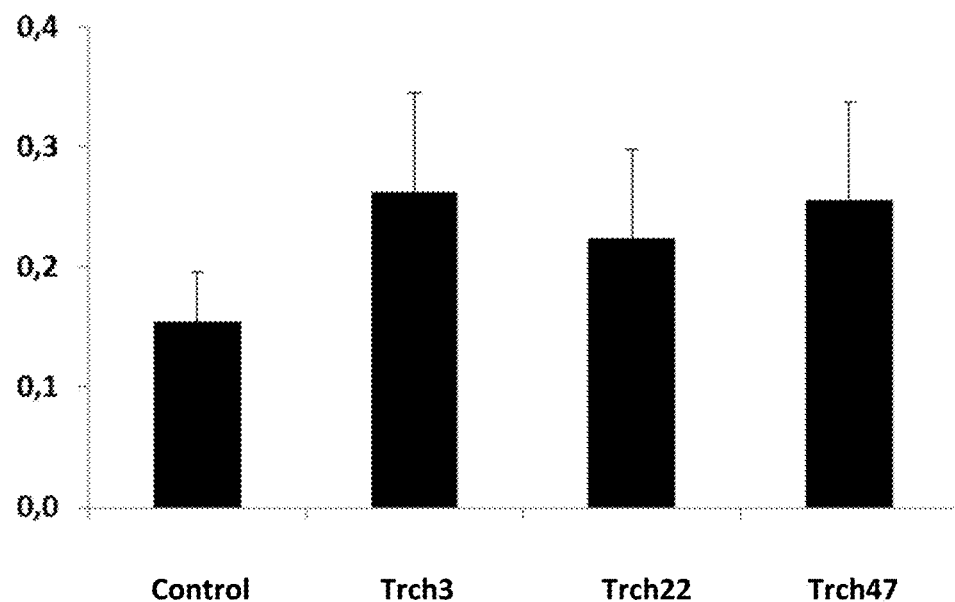
FIG. 3. Determination of weight of second trifoliate leaf of control plants and plants treated with the inoculants of Trch3, Trch22 and Trch47. The experimental data indicate the average weight of the trifoliate leaf measured in at least five replicates. Error bars indicate the measurements standard deviation.

In the same assays, a significant increase in seedling vigor and development was also detected, suggesting that strains additionally have beneficial effects on the growth rate of inoculated plants (estimated based on the development of the second plant trifoliate leaf) as shown in FIG. 3. These are critical results, as they emphasize the feasibility of the technological development and guarantee the effectiveness of the inoculant.

Example 3

Trichoderma-Bradyrhizobium Interaction Assay

Crops were established and grown in order to evaluate the growth capacity of both microorganisms: *Bradyrhizobiun japonicum* and *Trichoderma*.

Soybean plant nodulation capacity was also evaluated in the presence of *Trichoderma*, in comparison to control plants. These tests were conducted under controlled field crop conditions and allowed the assessment of the impact of fungal protection treatment on seeds, nodulation capacity, different growth parameters and final production of soybean.

Treatments were applied in first quality soybean. The experiment was implemented in the city of Pergamino, located to the north of the Buenos Aires province (33°57'51.87"S 60°34'36.89"W), on a Pergamino Series soil, typical Argiudol, mixed family, franca soil texture, thermal, Class 1-2, IP=85. The sowing was carried out with soybean variety DM 4615 STS, in rows spaced at 0.40 m. The experimental site registers a continuous agricultural rotation with several soybean crops in sequence. The ancestor was soybean. The base fertilization was carried out by applying 100 kg ha$^{-1}$ of a composition mixture (7-17-0 S5). Plots were kept completely free of weeds and pests.

The test was designed as follows: totally random blocks with four repeats and five treatments. The different treatments are detailed in Table 2, below.

TABLE 2

Seed treatment and soybean canopy growth—Pergamino field test

| | Seed treatment | Dose |
|---|---|---|
| T1 | Control | |
| T2 | Thiram + Carbendazim d1 | 1 ml kg$^{-1}$ |
| T3 | Thiram + Carbendazim d3 | 3 ml kg$^{-1}$ |
| T4 | *B. japonicum* + Trch3 (Bio-inoculant of the invention) | 1 ml kg$^{-1}$ |
| T6 | Metalaxyl + Fluodioxinil + Thiabendazole | 1 ml kg$^{-1}$ |

For this assay, number of nodules per plant, nodule size, localization and functionality were determined. According to the results obtained for this field test, plants treated with the *Trichoderma* isolate, a high number of large size nodules was obtained, also being functional. These nodules were mainly located within secondary roots. The number and quality of the nodules was higher in plants treated with the isolate as compared to plants treated with conventional chemical agents.

Regarding the physiological changes, plants treated with *T. harzianum* or with chemical fungicides displayed similar germination rate, nodules per plant, pod number, light interception, bean size and number. However, in treated-plants these values were significantly higher than those in control plants. Based on these results, biologically-treated plants demonstrated a performance similar to those chemically treated.

Figure 4:
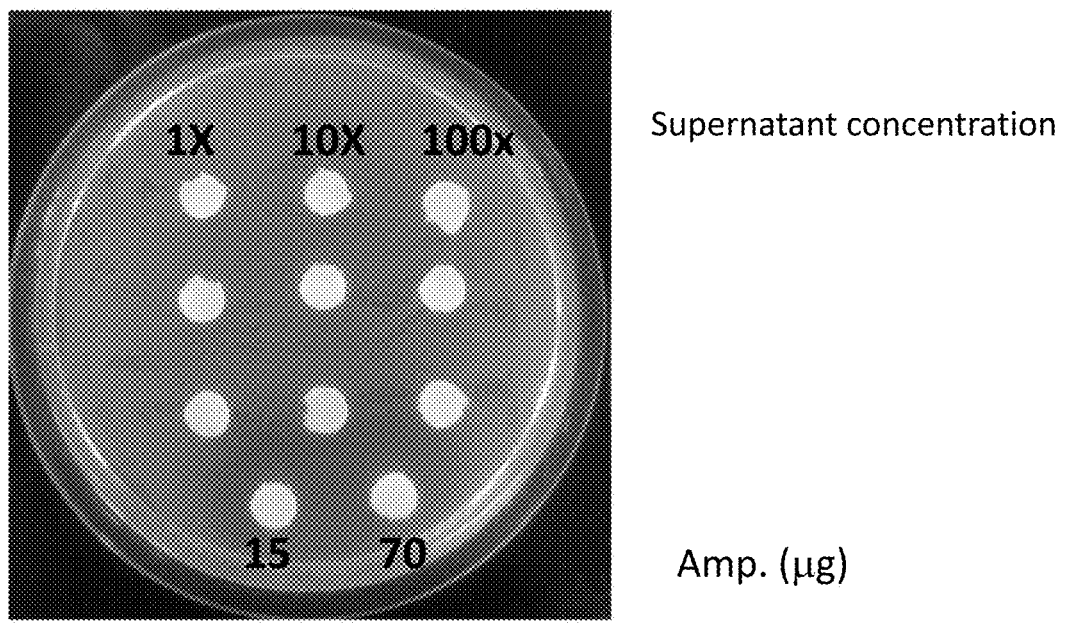
FIG. 4. Determination of compatibility between *Trichoderma* isolates and *Bradyrhizobium japonicum* was carried on by antibiogram assays with the fungal supernatant (at three different concentrations: 1×, 10× and 100×) disposed on *Bradyrhizobium japonicum* culture, using ampicillin at 15 and 70 μg in each paper disc. The inhibition halos were measured to demonstrate this compatibility.

Also, the effect of *Trichoderma* exudates on *B. japonicum* growth in vitro was assessed. Antibiogram assays were performed with filter paper discs saturated with fungal supernatant at different concentrations (1×, 10× and 100×), using the antibiotic ampicillin (containing 15 μg or 70 μg). They were disposed on a *B. japonicum* lawn and inhibition halos were determined (FIG. 4).

TABLE 3

Protection treatments on seeds using either chemical agents or biological inoculant in soybean. Plant number (15 days after sowing), Normalized Difference Vegetation Index (NDVI) by Green seeker, nodule and pod number, radiation interception and vigor are depicted.

| Treatment | No. of plants 15 d.a.s. | Green Seeker R4 ® | Nodes/ plant | Pod/plant | Interception (%) | Vigor |
|---|---|---|---|---|---|---|
| T1: Control | 31.3 | 0.86 | 10.0 | 40.0 | 79.1 | 3.0 |
| T2: ThC (1 ml/kg) | 32.1 | 0.86 | 11.5 | 46.5 | 79.4 | 3.1 |
| T3: ThC (3 ml/Kg) | 31.5 | 0.85 | 12.0 | 45.0 | 90.3 | 3.1 |
| T4: Bio-inoculant of the invention | 33.5 | 0.86 | 13.0 | 47.5 | 85.4 | 3.6 |
| T6: Met + Fluod + Thiab | 35.0 | 0.87 | 12.0 | 44.0 | 85.6 | 3.5 |
| R2 vs Yield | 0.88 | 0.58 | 0.68 | 0.42 | 0.29 | 0.86 |

ThC: Thiram + Carbendazim;
Bio-inoculant of the invention: *Bradyrhizobium japonicum* + *Trichoderma harzianum* (Trch3, strain PTA-125914, deposited at the ATCC on May 20, 2019).
Met: Metalaxyl;
Fluod: Fluodioxinil;
Thiab: Thiabendazole.

Example 4

Inoculant Efficiency on Soybean Crops in the Field

In this field test, the experiment was directed to the evaluation of the impact of different seed biological treatments over soybean crop productivity.

The test was designed as totally random blocks with four repeats and six treatments (T1 control and T2-T6 biological and chemical treatments). The different evaluated strategies are detailed in Table 4 below.

TABLE 4

Chemical and biological treatment on soybean seeds. Pergamino field assay.

| | Seed treatment | Dose |
|---|---|---|
| T1 | Control | |
| T2 | Thiram + Carbendazim d1 | 1 ml kg$^{-1}$ |
| T3 | Thiram + Carbendazim d3 | 3 ml kg$^{-1}$ |
| T4 | *B. japonicum* + Trch3 (Bio-inoculant of the invention) | 1 ml kg$^{-1}$ |
| T5 | Commercial product | 6 ml kg$^{-1}$ |
| T6 | Metalaxyl + Fluodioxinil + Thiabendazole | 1 ml kg$^{-1}$ |

Commercial product: Rizoderma ™

All samples were firstly treated with 3 ml/kg of *B. japonicum* at a concentration of 10$^9$ CFU/ml and amended with each one of the treatments. In the case of the commercial biological product, the recommendations of the manufacturer were followed using a dose of 6 ml/kg of seed, at a concentration of 2×10$^8$ CFU/ml of *T. harzianum* strain Th2. However, the bio-inoculant of this invention only contained 2×10$^8$ UFC/ml of *T. harzianum* Trch3 and was applied at a dose of 1 ml/kg of seeds.

The experiment was carried out at an agricultural experimental station in the city of Pergamino, located to the north of the Buenos Aires province (33°57'51.87"S 60°34'36.89"W), on a Pergamino Series soil, typical Argiudol, mixed family, franca soil texture, thermal, Class 1-2, IP=85.

The sowing was carried out with soybean variety N4619 RG STS Ipro, in rows spaced at 0.40 m. The experimental site registers a continuous agricultural rotation with a high intensification level and crop rotation. Insecticides and fungicides were applied during the treatment cycle for preventing attack by bollworm moth and chinch bug as well as other plant diseases. Plots were kept completely free of weeds and pests. A base fertilization was carried out by applying 80 kg ha$^{-1}$ of a composition mixture (10-40-0-S9). Seeds in all the different treatment lots were inoculated with *Bradyrhizobium japonicum*, apart from those being specifically tested.

Plants emerged 15 days after sowing were recounted. NDVI was determined on growing stage R4 by means of Green seeker sensor and radiation interception. Also, nitrogen content was estimated by measuring chlorophyll with a Minolta Spad 502, and plant vigor was qualified as a function of the general state of the plot, its uniformity and sanity. Nodulation was evaluated considering number, weight, size and localization of the nodules. A harvest sample was used for determining: yield components, nodule number, pod number, NG (grain number) and PG (grain weight). Results were assessed by variance partition, mean comparison and regression analysis.

Table 5 below depict the variables for nodulation, while Tables 6 and 7 show the yield, its components and other parameters determined during the crop cycle.

TABLE 5

Quantitative and qualitative evaluation of nodulation. Treatments on seeds with nitrogen-fixing bacteria, chemical fungicides and the plant growth promoter Trichoderma harzianum in soybean. INTA Pergamino, field assay. 10 plants per lot were evaluated in the 4 repeats.

| T | Treatments | Nodule number (1) | Nodule size (2) | Local-ization (3) | Func-tionality (4) |
|---|---|---|---|---|---|
| T1 | Control | 2 | 2 | 2 | 3 |
| T2 | Thiram + Carbendazim d1 | 3 | 2 | 3 | 3 |
| T3 | Thiram + Carbendazim d3 | 3 | 2 | 4 | 3 |
| T4 | B. japonicum + Trch3 (Bio-inoculant of the invention) | 2 | 3 | 3 | 3 |
| T5 | Commercial product | 4 | 3 | 4 | 2 |
| T6 | Metalaxyl + Fluodioxinil + Thiabendazole | 3 | 3 | 2 | 3 |
| | $R^2$ vs yield | 0.06 | 0.62 | 0.16 | 0.12 |

Commercial product: Rizoderma ™

[1]Nodule number: 1: null, 2: scarce, 3: medium, 4: high, 5: very high.
[2]Nodule size: 1: very little, 2: little, 3: medium size, 4: large size, 5: very large size.
[3]Localization: 1: totally in secondary roots, 2: mostly in secondary roots, 3: equal distribution in main root: secondary root, 4: mostly in main root, 5: nodules totally located in main root.
[4]Functionality: 1: completely green or brown tonality, 2: mostly green or brown tonality, 3: diverse tonality, 4: mostly redish tonality, 5: redish tonality in all nodules.

TABLE 6

Plant density (plants per m$^2$), NDVI as measured by Green seeker, nodule and pod number, radiation interception, vigor, plant height (cm), Nitrogen content as estimated by Spad, grain yield, components and response over control. Treatments on seeds with nitrogen-fixing bacteria, chemical fungicides and the plant growth promoter Trichoderma harzianum in soy. Pergamino, field assay.

| Treatment | Plant density | Green Seeker R4 | Nodules/ plant | Pods/ plant | [1]Interception R4 (%) | [2]Vigor |
|---|---|---|---|---|---|---|
| Control | 24.5 | 0.81 | 15.0 | 58.0 | 87.8 | 3.5 |
| Thiram + Carbendazim d1 | 25.5 | 0.84 | 17.5 | 60.0 | 87.8 | 3.8 |
| Thiram + Carbendazim d3 | 22.4 | 0.83 | 16.0 | 67.5 | 87.7 | 3.8 |
| B. japonicum + Trch3 (Bio-inoculant of the invention) | 24.1 | 0.83 | 16.5 | 68.5 | 89.0 | 3.8 |
| Commercial product | 26.0 | 0.82 | 17.0 | 62.5 | 86.3 | 3.7 |
| Metalaxyl + Fluodioxinil + Thiabendazole | 22.3 | 0.83 | 16.0 | 71.0 | 87.4 | 3.7 |
| $R^2$ vs Yield | 0.01 | 0.33 | 0.36 | 0.32 | 0.02 | 0.45 |

Commercial product: Rizoderma ™
[1]Interception: evaluated as % of maximum incident radiation.
[2]Vigor index: according to the following score 1: minimum - 5: maximum. It evaluates sanity, plant size and lot uniformity.

TABLE 7

Plant height (cm), nitrogen content as estimated by Spad, bean yield, components and response over control. Treatments on seeds with nitrogen-fixing bacteria, chemical fungicides and the plant growth promoter Trichoderma harzianum in soybean. Pergamino, field assay.

| Treatment | Plants height (cm) | Spad at R3 | Yield (kg ha$^{-1}$) | Bean Yield (NG) | Bean Weight (PG) | Diff vs Control (kg ha$^{-1}$) |
|---|---|---|---|---|---|---|
| Control | 97 | 45.1 | 3977.3 | 2840.9 | 140 | |
| Thiram + Carbendazim d1 | 96 | 47.3 | 4199.4 | 3065.2 | 137 | 222.1 |
| Thiram + Carbendazim d3 | 97 | 44.9 | 4174.2 | 3024.8 | 138 | 196.9 |
| B. japonicum + Trch3 (Bio-inoculant of the invention) | 98 | 45.4 | 4459.6 | 3303.4 | 135 | 482.3 |
| Commercial product | 97 | 45.5 | 4348.8 | 3245.3 | 134 | 371.5 |
| Metalaxyl + Fluodioxinil + Thiabendazole | 93 | 45.6 | 4248.1 | 3170.2 | 134 | 270.8 |

TABLE 7-continued

Plant height (cm), nitrogen content as estimated by Spad, bean yield, components and response over control. Treatments on seeds with nitrogen-fixing bacteria, chemical fungicides and the plant growth promoter *Trichoderma harzianum* in soybean. Pergamino, field assay.

| Treatment | Plants height (cm) | Spad at R3 | Yield (kg ha$^{-1}$) | Bean Yield (NG) | Bean Weight (PG) | Diff vs Control (kg ha$^{-1}$) |
|---|---|---|---|---|---|---|
| R$^2$ vs Yield | 0.02 | 0.01 | | 0.97 | 0.70 | |
| P = | | | 0.08 | | | |
| CV (%) | | | 4.94 | | | |

Commercial product: Rizoderma ™

Growth stages (R3, R4, or R5) were established following by Fehr and Caviness definitions (Fehr, W. R., Caviness, C. F., Burmood, D. T., Pennington, J. S., 1971. *Stage of development descriptions for soybeans, Glycine max (L.) Merrill*. Crop Sci. 11, 929-931).

Figure 5:
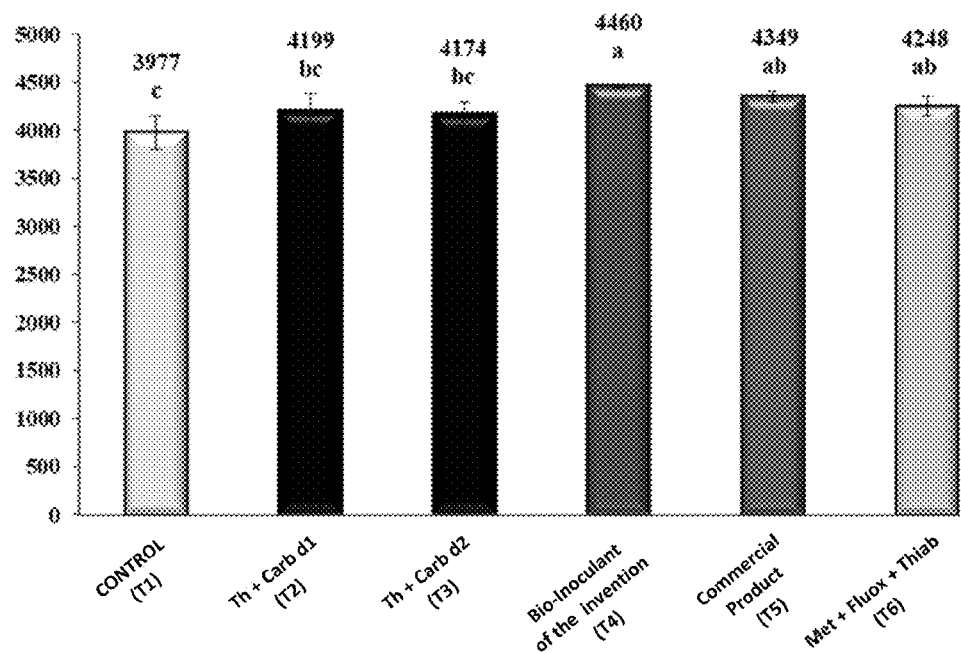
FIG. 5. Grain yield according to different biological and chemical treatments (T1: control; T2 and T3: chemical fungicides (Thiram+Carbendazim at different doses d1 and d2, respectively); T4: bio-inoculant of the invention; T5: commercial product Rizoderma™; and T6: complete fungicide Metalaxyl+Fludioxinil+Thiabendazole) on soybean seeds in a field assay in the agricultural experimental station (city of Pergamino, Buenos Aires, Argentina). Different letters over the columns represent significant differences among treatments (Fishers Least Significant Difference (LSD) a=0.10, yield$_{LSD}$=259.5 kg ha$^{-1}$). Error bars indicate standard deviation.

Beans yield assessment was determined after soybean seeds were subjected to biological treatments. The results obtained for the field assay in Pergamino are illustrated in FIG. 5.

Although rainfalls were scarce during the field assay described in this Example, the yield components were able to be sustained. Both the initial reserve and the rainfalls by the end of the cycle allowed a moderate impact on hydric stress. Yields achieved a mean of 4234.6 kg ha$^{-1}$ (Table 7 and FIG. 5), being acceptable for the environmental conditions of the year.

Differences among yields were statistically significant (P=0.08; cv=6.9%). A set of three treatments, namely: *B. japonicum*+Trch3 (the bio-inoculant of the invention, T4), Commercial product (T5) and the complete fungicide Metalaxyl+Fludioxinil+Thiabendazole (T6) achieved maximum yield, exceeding the control (T1) and, in the case of treatment with the bio-inoculant of the invention (*B. japonicum*+Trch3) also exceeding the chemical fungicides (T2 and T3).

Nodulation had a medium to good quality. Clearly, the lack of rainfall limited plant nodulation. Treatments inoculated with *Trichoderma harzianum* (T4 and T5) presented a better nodulation than its controls (Table 5). Size and—to a lesser extent—nodule localization, were the most representative variables (Table 5).

It can be clearly seen that the use of *Trichoderma*, besides its function as a pathogen controller, is also capable of stimulating growth and enhancing some of the main yield components. More precisely, as measured by the determination coefficient (r2), those variables better explaining the obtained yields were NG (r2=0.97), PG (r2=0.70), nodules size (r2=0.62), vigor qualification (r2=0.45) and nodule per pod (nodule pod$^{-1}$) number (r2=0.36) (Tables 5, 6 and 7).

According to the results obtained in the field assay described in this example, the biological treatment used in soybean leads to an important enhancement in several crop parameters, showing a high compatibility of the microorganisms comprised in the inoculum of the invention, *Trichoderma harzianum* and *Bradyrhizobium japonicum*. This new fertilization strategy allowed a crop increase of up to 482.3 kg ha$^{-1}$ as compared to classical phosphorus-sulfur (PS) fertilization.

It should be noted that the biological inoculant of the invention generated better results in comparison with the reference bio-pesticide (commercial product Rizoderma™) even in a 6-fold lower dose concentration, thus showing an enhanced effect of the formulation.

Example 5

Molecular Analysis of the Mode of Action of the Bio-Inoculant of the Invention

The molecular analysis of the mode of action of the bio-inoculant of the invention was performed by differential proteomics by using Label Free Quantitation analysis technique, in order to molecularly identify which are the mechanisms that lead to a pre-activation state of the plant defense systems as a consequence of the treatment with the bio-inoculant of the present invention. On the other hand, the accumulation of said defense metabolites was measured.

Differential proteomics studies allow an analysis of the group of proteins that are affected in two different situations when comparing soybean plants infected with *Cercospora sojina* (pathogen responsible of producing "frog eye spot" disease in soybean crops): in one case an initial treatment with the bio-inoculant of the invention was performed previous to the inoculation with the pathogen and in the other case the direct inoculation with the pathogen was done without treatment with the bio-inoculant of the invention. Both controls were further done as described in Table 8.

TABLE 8

Treatments.

| | Control | Pathogen | Bio-inoculant of the invention | Bio-inoculant of the invention + Pathogen |
|---|---|---|---|---|
| Bio-inoculant of the invention | − | − | + | + |
| *Cercospora sojina* | − | + | − | + |

For this study, 12 soybean plants inoculated at sowing with the inoculant of this invention were used in each treatment. Nine days after germination plants were infected with *Cercospora sojina*, the foliar pathogen responsible for eye frog disease. Leaf samples were collected three days post infection for protein analysis. The conditions used for this study are summarized in Table 8 above. Two leaves per plant of each group under study were frozen in liquid $N_2$ and grounded with mortar and pestle. A 0.5 g leaf powder sample was further processed for its study.

The protocols followed for the different assays are described below:

Protein Extraction

A biological extract was obtained from the 0.5 leaf treatment with 1 ml of extraction buffer [BE: CHAPS (4% p/v), EDTA (10 mM), protease inhibitors (SigmaFast, Sigma Aldrich), in Tris-HCl (100 mM, pH=8.0)]. Then, the insoluble vegetal material was eliminated by centrifugation at 4° C. for 30 minutes at 15000 rpm. 200 µL supernatant aliquots were conserved for freezing at −20° C.

Acetone Protein Precipitation

The protein content in 200 µl aliquots of each extract was precipitated with 1 ml of cold acetone (−20° C.). They were incubated during 2 hours at −20° C. and a 30 minutes centrifugation at 4° C. and 15000 rpm was performed. The obtained precipitate was washed twice with 1 ml of cold acetone (−20° C.). The precipitated proteins were dissolved in 200 µl of BE and the insoluble material was eliminated by centrifugation at 4° C. during 30 minutes at 15000 rpm. The protein extract was conserved at −20° C.

Analysis by Liquid Chromatography Coupled to Mass Spectrometry

Each of the samples, analyzed in triplicate, underwent a trypsin enzymatic digestion.

Then, 2 µg of said digested was subjected to a liquid nanocromatography coupled to mass spectrometry in tandem.

A C18, 2 µm, 100 A, 50 µm×150 mm [Thermo Scientific, Easy-Spray ColumnPepMap RSLC (P/N ES801)] column was used using the EASY-nLC 1000 system of Thermo Scientific, and Q-Exactive Thermo Scientific mass spectrometer.

Figure 6:
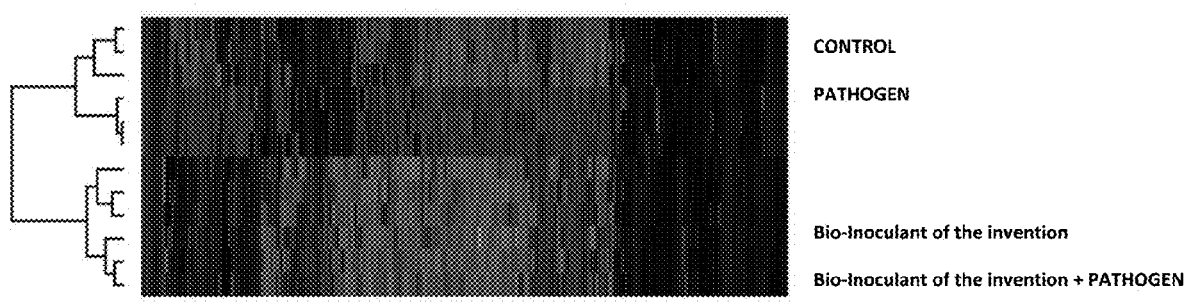
FIG. 6. Hierarchical grouping of all samples showing the set of proteins expressed in control and treated plants, in absence or presence of the pathogen. The pathogen used in this experiment as a model patho-system was *Cercospora sojina*. This study was carried out in triplicate.

A first analysis of the results demonstrated the differential effect of the bio-inoculant of the present invention on soybean plants at the molecular level. A dendrogram is shown in FIG. 6, which clearly shows a differential protein profile between control and pathogen treatments (Table 8). Nonetheless, such difference is not as evident when comparing uninfected and infected plants when the latter had been previously treated with the bio-inoculant of the invention. These results show that the inoculation with the inventive bio-inoculant stabilizes crop metabolism against a *C. sojina* attack.

The hierarchical grouping of all samples showing the set of proteins expressed in the tested plants reveals a greater similarity between the plants previously treated with the bio-inoculant of the invention and those plants that were not inoculated, respectively. Based on proteomic analysis, infected and non-infected plants treated with the inventive bio-inoculant displayed a close relationship in the hierarchical tree, suggesting a reduction of the severity of the effects of the pathogen as a consequence of the protective effect of the bio-inoculant of the invention.

Figure 7:
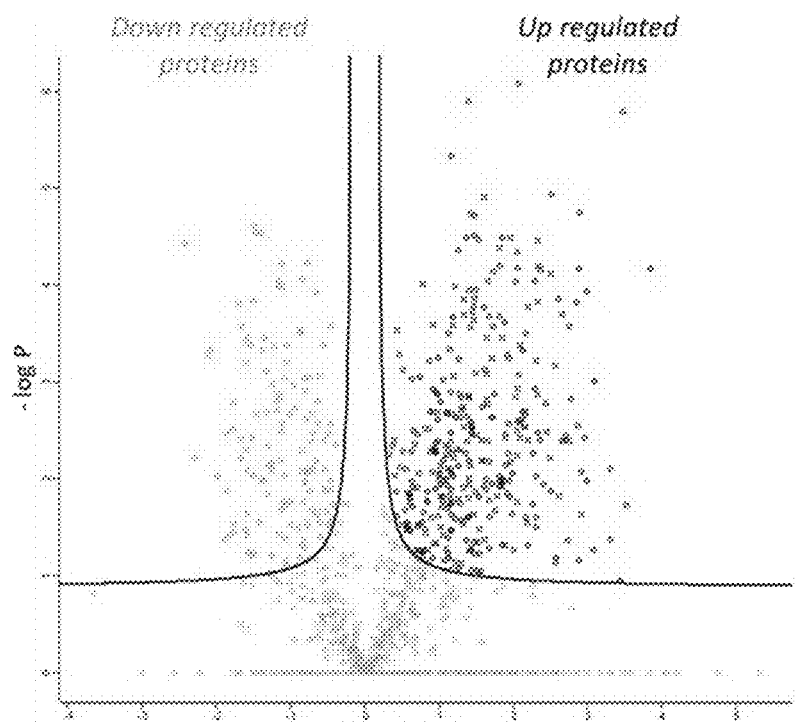
FIG. 7. Statistical analysis (t-test, FDR=0.05) of differential proteomic results from pathogen-infected crops illustrated as a volcano plot, showing two groups of proteins: one is quantitatively increased (up-regulated) while the other group is decreased (down-regulated). Each protein group belongs to different functional clusters.

When performing a statistical analysis of the proteomic results from crops infected with the pathogen (with and without treatment with the inventive bio-inoculant, respectively) two groups of proteins could be differentiated, one that is quantitatively increased (up-regulated) and the other diminished (down-regulated). Each of these two protein sets were grouped in functional clusters. A volcano plot illustrating these two groups of proteins is shown in FIG. 7.

Based on this analysis, the present inventors were able to establish in a precise way the existence of a differential pattern in the routes and cellular mechanisms involved in the pre-activation of the defense processes of the plant against pathogenic agents when the seeds are previously treated with the bio-inoculant of the invention.

Example 6

Evaluation of the Accumulation of Defense Metabolites in Soybean Plants

Figure 8:
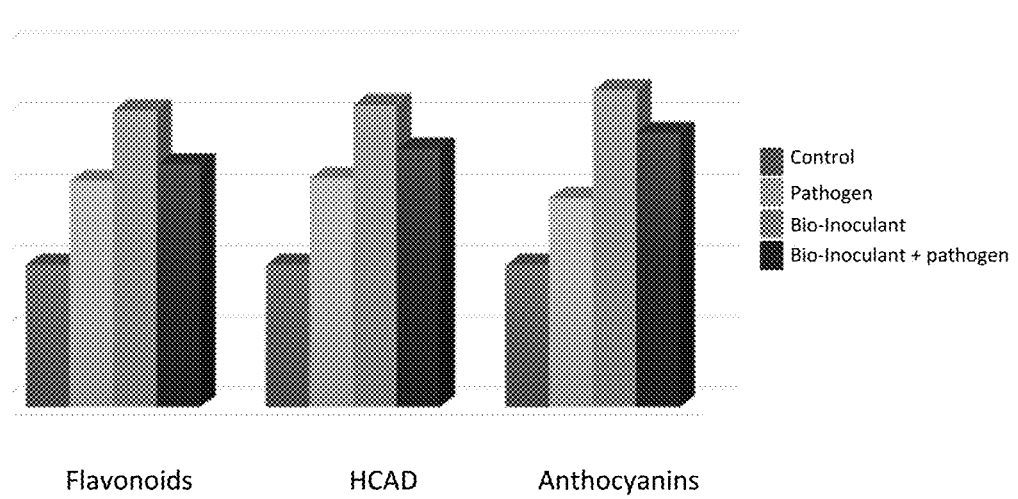
FIG. 8. Evaluation of the accumulation of defense-related metabolites: flavonoids, hydroxycinnamic acid derivatives (HCAD) and anthocyanins in treated and control plants. Bars in different shades of gray represent the four conditions studied (control, pathogen, bio-inoculant of the invention and bio-inoculant+pathogen). Three plants of each condition were used for this assay.

A methanolic extract was obtained by first treating 0.5 g leaves powder of each of the treatments depicted in Table 8 of Example 5 above, with 3 ml of acidic methanol (1% HCl), followed by incubation at room temperature for 8 hours and two minutes centrifugation at 3,000×g. Subsequently, defense metabolites present in the supernatant were measured by spectrometry, measuring the absorbance at 320 nm, 360 nm and 517 nm for determining flavonoids, hydroxycinnamic acid (HCAD) derivatives and anthocyanins respectively. Thus, the relative values thereof were determined with respect to the control (FIG. 8).

When evaluating the accumulation of defense metabolites, the results obtained correlate with what was observed by proteomics analysis. As expected, synthesis of defense metabolites is activated following pathogen infection; however, a previous inoculation with the bio-inoculant of the present invention enables the plant with an enhanced defensive response having higher levels of antimicrobial metabolites.

SEQUENCE LISTING

SEQ ID NO: 1
>Trch3
TGTGAACGTTACCAAACTGTTGCCTCGGCGGGATCTCTGCCCCGGGTGCG
TCGCAGCCCCGGACCAAGGCGCCCGCCGGAGGACCAACCAAAACTCTTAT
TGTATACCCCCTCGCGGGTTTTTTTATAATCTGAGCCTTCTCGGCGCCTC
TCGTAGGCGTTTCGAAAATGAATCAAAACTTTCAACAACGGATCTCTTGG
TTCTGGCATCGATGAAGAACGCAGCGAAATGCGATAAGTAATGTGAATTG
CAGAATTCAGTGAATCATCGAATCTTTGAACGCACATTGCGCCCGCCAGT
ATTCTGGCGGGCATGCCTGTCCGAGCGTCATTTCAACCCTCGAACCCCTC
CGGGGGGTCGGCGTTGGGGATCGGCCCTGCCTTGGCGGTGGCCGTCTCCG
AAATACAGTGGCGGTCTCGCCGCAGCCTCTCCTGCGCAGTAGTTTGCACA
CTCGCATCGGGAGCGCGGCGCGTCCACAGCCGTTAAACACCCAACTTCTG
AAATGTTGACCTCGGATCAGGTAGGAATACCCGCTGAACTTAAGCATATC
AAAAA SEQ ID NO: 2
>Trch22
TGTGAACGTTACCAAACTGTTGCCTCGGCGGGATCTCTGCCCCGGGTGCG
TCGCAGCCCCGGACCAAGGCGCCCGCCGGAGGACCAACCAAAACTCTTAT
TGTATACCCCCTCGCGGGTTTTTTTATAATCTGAGCCTTCTCGGCGCCTC
TCGTAGGCGTTTCGAAAATGAATCAAAACTTTCAACAACGGATCTCTTGG
TTCTGGCATCGATGAAGAACGCAGCGAAATGCGATAAGTAATGTGAATTG
CAGAATTCAGTGAATCATCGAATCTTTGAACGCACATTGCGCCCGCCAGT
ATTCTGGCGGGCATGCCTGTCCGAGCGTCATTTCAACCCTCGAACCCCTC
CGGGGGGTCGGCGTTGGGGATCGGCCCTGCCTTGGCGGTGGCCGTCTCCG
AAATACAGTGGCGGTCTCGCCGCAGCCTCTCCTGCGCAGTAGTTTGCACA
CTCGCATCGGGAGCGCGGCGCGTCCACAGCCGTTAAACACCCAACTTCTG
AAATGTTGACCTCGGATCAGGTAGGAATACCCGCTGAACTTAAGCATAAG
AAAAA SEQ ID NO: 3
>Trch47
TGTGAACGTTACCAAACTGTTGCCTCGGCGGGATCTCTGCCCCGGGTGCG
TCGCAGCCCCGGACCAAGGCGCCCGCCGGAGGACCAACCAAAACTCTTAT
TGTATACCCCCTCGCGGGTTTTTTTATAATCTGAGCCTTCTCGGCGCCTC
TCGTAGGCGTTTCGAAAATGAATCAAAACTTTCAACAACGGATCTCTTGG
TTCTGGCATCGATGAAGAACGCAGCGAAATGCGATAAGTAATGTGAATTG
CAGAATTCAGTGAATCATCGAATCTTTGAACGCACATTGCGCCCGCCAGT
ATTCTGGCGGGCATGCCTGTCCGAGCGTCATTTCAACCCTCGAACCCCTC
CGGGGGGTCGGCGTTGGGGATCGGCCCTGCCTTGGCGGTGGCCGTCTCCG
AAATACAGTGGCGGTCTCGCCGCAGCCTCTCCTGCGCAGTAGTTTGCACA
CTCGCATCGGGAGCGCGGCGCGTCCACAGCCGTTAAACACCCAACTTCTG
AAATGTTGACCTCGGATCAGGTAGGAATACCCGCTGAACTTAAGCATATA
AATAA

The invention claimed is:

1. A biological inoculant, comprising:
   *Bradyrhizobium japonicum*; and
   a *Trichoderma harzianum* strain, comprising an 18S rRNA gene sequence selected from the group consisting of SEQ ID NO: 1, SEQ ID NO: 2 and SEQ ID NO: 3,
   wherein the *Bradyrhizobium japonicum* is formulated as a water-based extract and the *Trichoderma harzianum* strain is added to the *Bradyrhizobium japonicum* extract as a conidial suspension having a final concentration of $10^6$-$10^9$ spores/ml.

2. The biological inoculant of claim 1, wherein the *Trichoderma harzianum* strain comprises an 18S rRNA gene sequence of SEQ ID NO: 1.

3. The biological inoculant of claim 2, wherein the *Trichoderma harzianum* strain is deposited at the American Type Culture Collection (ATCC) under Accession Number PTA-125914.

4. A method for protecting agricultural crop plants against infection by phytopathogenic fungi, the method comprising: applying the biological inoculant according to claim 1 to the seeds of agricultural crop plants before cultivation.

5. The method according to claim 4, wherein the crop plants are selected from the group consisting of soybean, wheat, maize, sunflower, cotton, sorghum, alfalfa, flax, canola, chickpea, rice, potato, onion, yerba mate), tea and vine.

6. The method according to claim 4, wherein the phytopathogenic fungi are selected from the group consisting of *Fusarium* sp., *Colletotrichum* sp., *Cercospora* sp., *Sclerotinia* sp., and *Rhizoctonia* sp.

* * * * *

SEQUENCE LISTING

<160> NUMBER OF SEQ ID NOS: 3

<210> SEQ ID NO 1
<211> LENGTH: 555
<212> TYPE: DNA
<213> ORGANISM: Trichoderma harzianum

<400> SEQUENCE: 1

| | |
|---|---:|
| tgtgaacgtt accaaactgt tgcctcggcg ggatctctgc cccgggtgcg tcgcagcccc | 60 |
| ggaccaaggc gcccgccgga ggaccaacca aaactcttat tgtataccccc ctcgcgggtt | 120 |
| tttttataat ctgagccttc tcggcgcctc tcgtaggcgt ttcgaaaatg aatcaaaact | 180 |
| ttcaacaacg gatctcttgg ttctggcatc gatgaagaac gcagcgaaat gcgataagta | 240 |
| atgtgaattg cagaattcag tgaatcatcg aatctttgaa cgcacattgc gcccgccagt | 300 |
| attctggcgg gcatgcctgt ccgagcgtca tttcaaccct cgaacccctc cggggggtcg | 360 |
| gcgttgggga tcggccctgc cttggcggtg gccgtctccg aaatacagtg gcggtctcgc | 420 |
| cgcagcctct cctgcgcagt agtttgcaca ctcgcatcgg gagcgcggcg cgtccacagc | 480 |
| cgttaaacac ccaacttctg aaatgttgac ctcggatcag gtaggaatac ccgctgaact | 540 |
| taagcatatc aaaaa | 555 |

<210> SEQ ID NO 2
<211> LENGTH: 555
<212> TYPE: DNA
<213> ORGANISM: Trichoderma harzianum

<400> SEQUENCE: 2

| | |
|---|---:|
| tgtgaacgtt accaaactgt tgcctcggcg ggatctctgc cccgggtgcg tcgcagcccc | 60 |
| ggaccaaggc gcccgccgga ggaccaacca aaactcttat tgtataccccc ctcgcgggtt | 120 |
| tttttataat ctgagccttc tcggcgcctc tcgtaggcgt ttcgaaaatg aatcaaaact | 180 |
| ttcaacaacg gatctcttgg ttctggcatc gatgaagaac gcagcgaaat gcgataagta | 240 |
| atgtgaattg cagaattcag tgaatcatcg aatctttgaa cgcacattgc gcccgccagt | 300 |
| attctggcgg gcatgcctgt ccgagcgtca tttcaaccct cgaacccctc cggggggtcg | 360 |
| gcgttgggga tcggccctgc cttggcggtg gccgtctccg aaatacagtg gcggtctcgc | 420 |
| cgcagcctct cctgcgcagt agtttgcaca ctcgcatcgg gagcgcggcg cgtccacagc | 480 |
| cgttaaacac ccaacttctg aaatgttgac ctcggatcag gtaggaatac ccgctgaact | 540 |
| taagcataag aaaaa | 555 |

<210> SEQ ID NO 3
<211> LENGTH: 555
<212> TYPE: DNA
<213> ORGANISM: Trichoderma harzianum

<400> SEQUENCE: 3

| | |
|---|---:|
| tgtgaacgtt accaaactgt tgcctcggcg ggatctctgc cccgggtgcg tcgcagcccc | 60 |
| ggaccaaggc gcccgccgga ggaccaacca aaactcttat tgtataccccc ctcgcgggtt | 120 |
| tttttataat ctgagccttc tcggcgcctc tcgtaggcgt ttcgaaaatg aatcaaaact | 180 |
| ttcaacaacg gatctcttgg ttctggcatc gatgaagaac gcagcgaaat gcgataagta | 240 |
| atgtgaattg cagaattcag tgaatcatcg aatctttgaa cgcacattgc gcccgccagt | 300 |
| attctggcgg gcatgcctgt ccgagcgtca tttcaaccct cgaacccctc cggggggtcg | 360 |
| gcgttgggga tcggccctgc cttggcggtg gccgtctccg aaatacagtg gcggtctcgc | 420 |

```
cgcagcctct cctgcgcagt agtttgcaca ctcgcatcgg gagcgcggcg cgtccacagc    480
cgttaaacac ccaacttctg aaatgttgac ctcggatcag gtaggaatac ccgctgaact    540
taagcatata aataa                                                     555
```